United States Patent [19]

Cook et al.

[11] Patent Number: 5,053,332

[45] Date of Patent: Oct. 1, 1991

[54] AGAROSE BEADS, PREFERABLY INCORPORATING BIOLOGICAL MATERIALS

[76] Inventors: Richard B. Cook, 156 Limerock, Rockland, Me. 04841; Richard B. Provonchee, 88 Mechanic St., Camden, Me. 04843; Samuel Nochumson, 6 Overlook Ave., Randolph, N.J. 07869

[21] Appl. No.: 383,520

[22] Filed: Jul. 24, 1989

[51] Int. Cl.[5] ..................... C12N 11/10; C08B 37/04
[52] U.S. Cl. .......................... 435/178; 536/3
[58] Field of Search ............... 435/178; 536/3

[56] References Cited

U.S. PATENT DOCUMENTS

| | | | |
|---|---|---|---|
| 3,423,397 | 1/1969 | Husaini | 530/3 |
| 4,208,482 | 6/1980 | Ehrenthal | 438/178 |
| 4,427,775 | 1/1984 | Chen et al. | 435/178 |
| 4,578,354 | 7/1986 | Cannon | 435/178 |
| 4,647,536 | 3/1987 | Mosbach et al. | 435/177 |
| 4,722,898 | 2/1988 | Errede et al. | 435/182 |
| 4,778,749 | 10/1988 | Vasington et al. | 435/2 |
| 4,891,319 | 1/1990 | Roser | 435/178 |

FOREIGN PATENT DOCUMENTS 854936  8/1981  U.S.S.R. .................... 536/3

OTHER PUBLICATIONS

Hjerten, S. *Biochim. Biophys. Acta* 1964, 79:393–398.
Bengtsson et al., S. *Biochim. Biophys. Acta* 1964, 79:399.
"Methods in Enzylmology" vol. 135 Part B, p. 399, Academic Press, 1987.
Nilsson et al., in "Preparation of Immobilized Animal Cells" [FEBS, 118: 145-150 (1980)].

*Primary Examiner*—J. E. Evans

[57] ABSTRACT

A method for forming agarose beads, which may incorporate biological material at least partially labile at above 40° C., in which an aqueous agarose solution is formed into bead-size portions which are gelled by contacting the portions with a cooled atmosphere, gas, and/or smooth hydrophobic surface, and then collected.

30 Claims, No Drawings

AGAROSE BEADS, PREFERABLY INCORPORATING BIOLOGICAL MATERIALS

BACKGROUND OF THE INVENTION

1. Field of the Invention

This invention relates to the formation of agarose beads, preferably incorporating biological materials such as mammalian cells or cellular components (organelles) in which the usefulness of the biological materials in laboratory and industrial processes is maintained after the formation process.

2. Statement of Related Art

There is increasing utilization of biological materials incorporated into algal polysaccharide gels in biotechnology. While the incorporation of biological materials in alginates and carrageenan, and the subsequent formation of beads are known in the art, the successful incorporation of biological materials as defined herein in agarose maintained at bioprocess grade without extraneous contamination has not previously been accomplished.

As used herein, the term "biological material(s)" includes material that is capable of self-replication either directly or indirectly. Representative examples include: bacteria; fungi including yeast; algae; protozoa; mammalian, especially eukaryotic cells; animal cell lines; hybridomas; plasmids; viruses; plant tissue cells; lichens; and seeds. "Biological material" also includes all cell segments and other non-living material of biological origin such as: proteins; enzymes and enzyme systems; vectors; and all organelles; as well as indirect replicating materials including: phages; plasmids; symbiants; and replication defective cells. All "biological materials" as defined in this invention are limited in that they are at least partially labile at 40° C. or above, especially at 37° C. or above. Eukaryotic cells are the preferred biological material in this invention, eukaryotic mammalian cells being particularly preferred.

Agarose has various desirable features over other gels, for example:

1. Agarose is clearer than other natural gelling media such as those requiring cations (e.g. alginates, carrageenan). As a result cells incorporated in agarose are more easily visualized, permitting easier differentiation.

2. Agarose does not require polymerization, as does hydroxyethylmethacrylate (HEMA) and polyacrylamide gel (PAG) both of which are used for cell culturing.

3 The presence of cations (notably calcium) used for formation of other types of gels influences cell proteins and cell metabolic functions and therefore is undesirable. Agarose does not contain such cations, since they are not utilized in its gelation.

4. Cells can be recovered from an agarose gel by a brief freeze/thaw process, which causes gel syneresis, without using the chelators normally required for alginate gels. Such chelators can adversely affect cell viability.

5. Agarose is a selective medium for transformed cells (e.g. hybridomas, certain tumor cells, and the like). It is a prerequisite for a cell line to be considered "transformed", that it be grown successfully, i.e., that it become "immortal".

There are, however, considerable difficulties in the formation of "beads" from agarose. The term "beads" is used herein in its normal biochemical laboratory sense, that is, as referring to small, discrete gel particles.

Agarose will only gel when cooled below its gelling temperature. It will not gel in response to cations such as calcium, which are effective for gelling alginate and some carrageenans. As a result, the earliest art describing the formation of agarose beads (for chromatographic application) used warm, non-aqueous solvents in which the agarose was emulsified before gel formation by cooling. There are numerous references to the formation of agarose beads, including: Hjerten, *S. Biochim. Biophys. Acta* 1964, 79:393–398; and Bengtsson et al., *S. Biochim. Biophys. Acta* 1964. 79:399, which teaches spraying the agarose into "ice-cold" ether. The use of organic solvents in agarose bead formation is still being utilized. The utilization of organic solvents in the formation of agarose beads renders such beads unsuitable for the incorporation of biological materials, since most such solvents are toxic to the cells at the concentrations in which they are used, and cannot satisfactorily be removed from the beads without damaging the incorporated material.

Another method for agarose bead formation, as disclosed in U.S. Pat. No. 4,647,536 is dropping an agarose emulsion into a cooled oil. Such a method is also disclosed in "Methods in Enzymology" Vol. 135 Part B, p. 401, Academic Press, 1987, which suggests the use of paraffin oil but cautions that the oil must be washed five times before use in order to remove any cytotoxins present in the oil. Therefore, after formation of the agarose beads using such procedure, they must be repeatedly washed and screened to free them of residual oil that would affect cell growth, enzyme production, etc. since, the presence of oil and/or solvent contamination renders agarose beads undesirable for biological material and particularly cell and cellular fragment entrapment.

U.S. Pat. No. 4,647,536 describes a general method for immobilization of animal and other cells in agarose and other reagents, and is incorporated herein by reference for its disclosure of such cells.

Nilsson et al., in "Preparation of Immobilized Animal Cells" [FEBS, 118:145–150 (1980)], discloses the formation of agarose beads incorporating a cell suspension by dissolving the agarose, admixing the cell suspension, and then pouring the mixture over a polytetrafluoroethylene plate which is "tightly covered with 3 mm holes". Another plate was used as a support and the two were held together by clamps. Nilsson et al., disclose that in the molding process, the agarose solidified into cylindrical beads. Nilsson et al., do not disclose any reason for using polytetrafluoroethylene as the mold form, and it can reasonably be assumed that it was used to facilitate extraction.

U.S. Pat. No. 4,722,898-Errede et al., discloses the immobilization of biological cells in a polytetrafluoroethylene matrix per se, and contrasts such material with the use of gelled polymers at column 2 line 47. The patent discloses the admixture of nutrient ingredients with the polytetrafluoroethylene matrix, including synthetic organic compounds derived from the polysaccharide dextran. There is, however, no disclosure of the use of agarose. A number of cells and microorganisms suitable for entrapment by the process of the subject invention are disclosed and, to the extent they are labile at 40° C. or above, that disclosure in U.S. Pat. No. 4,722,898 is incorporated herein by reference.

U.S. Pat. No. 4,778,749 - Vasington, et al., discloses the formation of hydrophilic gel beads incorporating mammalian cells and hybridomas. The only gels for which there are examples or enabling disclosure are alginates, specifically sodium alginates, which are gelled by the addition of a calcium salt. There is a statement at column 3, lines 39-42 that "other hydrophilic materials such as agarose, agar, carrageenan, xanthan gum, polyacrylamides, poly HEMA, and others known in the art can be used to advantage in particular environments". There is no further disclosure enabling the use of agarose, distinguishing agarose from the other listed materials, or recognizing that forming beads from agarose presents particular problems. This patent is incorporated by reference for its disclosures of biological materials capable of incorporation (entrapment) and for the formation of droplets of hydrogel/biological material aqueous solution, but not for the method of cooling (gelling) the droplets, which are contrary to the teachings of the present invention.

Of the various algal polysaccharides, whose gelation is not cation dependent, only agarose (and agar) will remain liquid at a temperature below 40° C., preferably 37° C., the temperature above which the viability of the biological materials, especially mammalian cells, becomes impaired. For this reason, agarose is a very desirable medium for the incorporation of living cells and viable cell fragments and subsequent bead formation. It is much preferred over agar because of its higher purity.

However, when such cellular material is incorporated in agarose and bead formation is attempted by the known bead formation method of dropping particles into cold (0°-25° C.) water, the result is totally unsatisfactory. Liquefied agarose dropped into cold water results in the formation of particles having unknown gel concentration, gradients, irregular surfaces and erratic geometry, any one of which is very undesirable.

The problems presented by prior art processes for the formation of agarose beads incorporating biological materials are, in summary:

(A) using gels which require maintenance at a temperature of over 40° C., especially over 37° C. to remain in a liquid state (i.e., which gel at about 40° C.), which temperature at least partially destroys the incorporated biological materials as defined herein;

(B) the presence of organic solvents and/or of oil contaminants as a result of the bead formation process; and/or (C) the inability to produce beads having regular surfaces and geometry, known gel concentration, and little or no concentration gradient. [Bead irregularity (e.g. the presence of appendages such as tails, skirts, etc.) is a problem because such appendages break-off and clog downstream filters, as well as loosen some incorporated cells which themselves can become a contaminant.]

SUMMARY OF THE INVENTION

This invention affords a general method for the production of agarose beads incorporating biological materials such as cells, cell fragments, microorganisms, and other complex proteins, which are labile (i.e. subject to heat degradation) at temperatures above 40° C., particularly above 37° C. The methods of this invention avoid contamination by materials which interfere with cell growth or reduce the biological effectiveness of the incorporated matter, such contaminants including oils, organic solvents, and metal cations such as calcium. The methods of this invention also afford agarose beads which have a sufficiently regular surface to permit unhindered visual observation, little or no gel concentration gradient, and, preferably, can be produced in a substantially uniform size and configuration.

The general method of this invention comprises forming agarose beads incorporating biological material at least partially labile at above 40° C. by the steps of:

A) forming an aqueous solution comprising an agarose which gels at a temperature of about 40° C. or less;

B) cooling the agarose solution to 40° C. or less while maintaining it in liquid form;

C) admixing an aqueous broth containing biological material which is at least partially labile at above 40° C. with the gel solution, to form a liquid agarose/broth mixture;

D) forming bead-size portions of the liquid agarose/broth mixture;

E) contacting said portions with a cooled atmosphere, gas, and/or smooth hydrophobic surface and maintaining such contact until said portions gel into formed agarose beads containing biological material; and F) collecting the formed beads.

There are various preferred embodiment groupings by which above steps D, E, and/or F may be effected, as follows.

EMBODIMENT I

DISCOID BEADS

A sheet of smooth hydrophobic material is perforated with uniformly sized round holes the approximate diameter of the beads to be formed and, in step D, the sheet is immersed into the agarose/broth mixture and then withdrawn, so that portions of the mixture are retained as menisci within the holes. Step E is effected by placing the sheet containing the retained mixture in a cooled atmosphere, and step F is effected by subjecting the gelled beads to a positive pressure on one side of the sheet, thereby forcing the disk-shaped beads out of the holes, after which they are collected in a container which may, optionally, contain water at room temperature.

The size/weight of beads produced by the methods of this invention are not limited, except by the means for dispensing the agarose or agarose/broth mixture drops. Thus, sizes of 0.05 to 1.0mm diameter, preferably 0.2 to 0.6mm diameter are contemplated. Independently of size, weights of 10 micrograms up to 50 milligrams, especially 5 to 20 milligrams are contemplated.

EMBODIMENT II HEMISPHERIC BEADS PLANAR HYDROPHOBIC SURFACE

In Step D, small drops of agarose/broth mixture are dispensed from a pipette, hypodermic needle, or the like, positioned above the top of a hydrophobic surface, or by dipping a needle or rod in the mixture and then touching the point or end to the top of a hydrophobic surface. Step E is effected by cooling the hydrophobic surface itself, such as by exposing its bottom to a cold fluid such as ice water. The formed agarose beads are then collected in Step F, by various means, including: (a) gently scraping a doctor blade across the surface; (b) inclining the hydrophobic surface and permitting the beads to slide off; (c) inclining the hydrophobic surface and removing the beads with a directed water wash; (d) flexing the hydrophobic surface (when it comprises a flexible material) to loosen the beads and then inclining the surface to permit the beads to slide and/or tumble off; or (e) bending the hydrophobic surface (when it comprises a flexible material) to form a chute, and inclining the chute to permit the beads to slide/tumble or be washed off, or forming the surface into a cone.

It is generally preferable that the hydrophobic surface be horizontal at the time the drops are applied, to prevent the formation of beads with tails [see Principles of Colloid and Surface Chemistry, supra at FIG. 6.8]. While the formed beads may generally be described as "hemispheric", it will be appreciated that as used herein, this term refers to spheres truncated by the plane of the hydrophobic surface, which hemispheroids may be flattened by gravity to approach a discoid shape, depending upon the agarose/broth mixture viscosity and speed of gelling from sol.

EMBODIMENT III

HEMISPHERIC BEADS

CYLINDRICAL HYDROPHOBIC SURFACE

For step D, small drops of agarose/broth mixture are dispensed in the same manner as in Embodiment II. However, for step E, a cylindrical hydrophobic surface is employed rather than a planar surface. The cylinder outside surface should be smooth, and if not already hydrophobic, it should be coated or laminated with a hydrophobic material. The cylinder is preferably hollow and internally cooled. In use, the cylinder is rotated about its central axis, which should be horizontal, and the drops are dispersed to the hydrophobic cylindrical surface at its highest point. The cylinder is then rotated up to 180° about its axis, with the speed of rotation and/or temperature of the hydrophobic cylinder surface such that gel beads are formed prior to completion of the rotation. The beads are collected, in step F, either by dropping under force of gravity into a container (preferably filled with water), or by removal with a biasing element such as doctor blade.

EMBODIMENT IV

SPHERICAL BEADS

For step D, small drops of agarose/broth mixture may be dispensed in the same manner as in Embodiment II, may be sprayed from a nozzle or pulsating jet, generated by a controlled drip, or the like (the use of a sonic nozzle for bead formation is disclosed in U.S. Pat. No. 4,399,219, which is incorporated herein by reference). Regardless of the means for dispensing, in step E, the drops are permitted to free fall against an upward current of cooled gas, and remain suspended at least until they gel. The temperature of the gas, as well as its velocity and density, will determine the speed at which the agarose/ broth mixture drops coagulate into generally spheroidal agarose beads. It is best to contain the gas in a defined space, such as a cooling tower, so that the above factors can be controlled and so that a regular flow pattern can be maintained. The cooled gas can be any one that is inert to the agarose/broth mixture, clean air being preferred. The cooling tower itself is not limited as to dimensions, and typically can be a hollow cylinder, into which the drops are introduced (preferably at the top), and which has an upward flow of cooling gas. If step E is run as a batch method, the gas flow can be stopped when the beads have gelled, and the beads collected at the bottom of the tower. If step E is run as a continuous method, the gas flow rate can be adjusted so that the drops/beads continually fall to the bottom at a controlled velocity, and are then collected (step F). As usual, they can be collected in water, if desired, since the gel beads will not redissolve at the cooled temperature.

EMBODIMENT V

BEADS WITHOUT INCORPORATED MATERIAL

It should be understood that the same methods disclosed herein for agarose beads incorporating biological material also could be used for the formation of beads of agarose per se, simply by eliminating the incorporation step. In such instance, the gelling temperature of the agarose is not important, and "normal" agarose or "high gel temperature agarose" may be employed. It should be obvious that the temperature constraints caused by the labile nature of the incorporated material will not apply, but all of the remaining constraints as to bead formation remain applicable. This embodiment therefore does not direct itself to solving the difficult problem of incorporating biological material at least partially labile at 40° C. above.

EMBODIMENT VI

LARGE SCALE PRODUCTION

It also should be understood that there is no known physical impediment to scaling-up the production of agarose beads according to any of Embodiments I through V, and it is contemplated within this invention that such scale-up can be accomplished with minimal additional work, well within the capabilities of one of ordinary skill in the pertinent art.

The various devices that can be utilized for the several steps, such as the means for dispensing the drops, drop receiving surface, means for cooling the hydrophobic surface, and means for collecting the formed beads, comprise numerous embodiments, some of which are herein illustrated. The general conception of the inventive process is not limited as to specific apparatus or means, except that (A) the agarose must remain a sol (i.e., liquid) at 40° C. or less, preferably 37° C. or less, most preferably 30° C. or less; (B) the surface receiving the drops of aqueous agarose/broth mixture must be sufficiently hydrophobic to permit the drops to "bead" and not spread out; and (C) the receiving surface and/or ambient atmosphere must be sufficiently cold to cause rapid gelation of the agarose.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The agarose suitable for use in this invention must be one which gels at a low temperature and is of sufficient purity to be suitable for use in biotechnological processes (i.e. "bioprocess grade"). Since agarose is a "derivatized" naturally occurring marine colloid, the specific polysaccharide polymers contained therein are variable. It is critical that the agarose used in the present invention has a gelling temperature of 40° C. or less, preferably 37° C. or less, most preferably less than 30°

C., typically in 1% w/v with water. Agarose with a higher gelling temperature will partially or completely destroy the biological material as herein defined. Suitable products of this type are commercially available and include SeaKem ® LE, ME, HE and HEEO agarose which has a gelling temperature in 1.5% concentration of 36° C. and a melting temperature of 93° C.; SeaPlaque ® agarose which has a gelling temperature of 28° C. for a 4.0% solution and a melting temperature of 65° C.; NuSieve ® agarose which has a gelling temperature of 28° C. for a 1% gel and a melting temperature of 65° C.; and SeaPrep ® agarose which has a gelling temperature of 15° C. for a 1% gel and a melting temperature of 48° C. "SeaKem", "SeaPlaque", "NuSieve", and "SeaPrep" are all trademarks of FMC Corporation, BioProducts Group, Marine Colloids Division. Of the above agarose products, SeaPlaque, NuSieve, and SeaPrep are preferred and SeaPlaque and SeaPrep are particularly preferred.

Part of the normal preparation for agarose gels is to (A) dissolve the agarose powder in water or buffer solution by heating to boiling; (B) assemble and warm gel casting apparatus to be used; (C) pour or inject the warm agarose solution; and (D) allow the agarose to cool and cure into a strong, rigid gel. For the purposes of this invention, it is critical that the biological material, which is usually in an aqueous broth or solution, and which is to be incorporated and formed into agarose beads, is added after the gel solution has been cooled to 40° C. or less, preferably 37° C. or less, most preferably 30° C. or less. Once the biological material is added and gently mixed with the agarose solution, the same care obviously must be taken of the mixture as would be taken of the biological material alone. This agarose/biological material mixture comprises the drops which are used in the inventive processes.

It should again be emphasized that agarose useful in the inventive process must have a low gelling temperature, it being noted that there is a substantial differential in these temperatures for different types and grades of agarose. For example, NuSieve ® GTG agarose, a product of FMC Corporation, and which is useful herein, has been specially developed for the fine resolution of small DNA fragments of less than 1,000 basepairs (bp). The low melting temperature is useful for enzymatic processing of nucleic acids directly in the remelted agarose, in particular legation and transformation. Other known applications for this particular product include the separation of doublestranded RNA and single-stranded RNA.

SeaPlaque ® agarose, a product of FMC Corporation, gels at ambient temperatures (less than 30° C.) and has a remelt temperature of 65° C. (dependent on concentration). It remains in the sol state at 37° C. for up to 16 hours. This facilitates the incorporation of heat labile substances as contemplated in this invention without worry of heat shock, or premature gelation. Rapid gelation will occur in less than 10 minutes at temperatures below 20° C. These properties of the SeaPlaque ® agarose make it particularly preferred in the processes of the subject invention, since it is possible to prepare an agarose sol at 65° C. or higher, reduce its temperature to 37° C. or less for a considerable period of time, during which biological material can be admixed without urgency, and thereafter form beads according to the inventive processes, by rapidly cooling the sol below 20° C. Since the melt temperature of SeaPlaque ® agarose is 65° C., beads incorporating the biological material will remain stable at ambient temperatures, after they have been produced.

SeaKem ® agarose, a product of FMC Corporation, is an acceptable agarose for some applications, but generally less preferred for use in the inventive processes, although it is an "all-purpose" medium for separation techniques, and is stated to have excellent gel strength, purity, gel clarity, and low ionic charge (for minimal non-specific binding). The excellent gel strength of SeaKem ® agarose which allows its use in horizontal, vertical and tube gel formats also permits the formation of more durable beads for cell culture. Its high gel clarity facilitates the visualization of incorporated cells, as well as immunoprecipitation bands, and its minimal non-specific binding is particularly important for immunodiffusion techniques.

Specific grades of SeaKem ® agarose, particularly LE, ME, and HE, have gelling temperatures of 36° C. at 1.5% aqueous solution, and therefore may be used in the processes of this invention. Other grades of SeaKem ® agarose having gelling temperatures of approximately 42° C. at the same concentration, have limited usefulness in this invention, since they gel at temperatures too high for the viability of most biological material to be incorporated.

Uses for SeaKem ® LE (low electroendosmosis value) grade agarose which are already known in the art include general cell culture [Ho, et al., "Agarose Medium for Bioassay of Antimicrobial Substances", *Phytopathology*, 70:764–766 (1980)], and for other chromatographic techniques. Agarose chromatographic beads produced from SeaKem ® LE agarose are also known, but such beads have been produced by prior art techniques and are outside the scope of the present invention.

A further description of agarose and illustrations of exemplary plant cells, animal cells, and protoplasts that previously have been incorporated in agarose, and which therefore are useful in the present invention, is as follows:

Agarose has shown superiority over unfractionated agar as a growth support and assay medium for a variety of microorganisms, including bacteria, fungi, yeasts, viral propagation cells, animal cells, and plant cells and protoplasts. While agars do contain variable amounts of agarose, they also contain a variety of anionic polysaccharides (agaropectins) in addition to other organic and inorganic impurities. The anionic polymeric components of agar often exert an inhibitory effect on the growth of a number of organisms, and the removal of these anionic inhibitors occurs during agarose production, eliminating this undesirable property. The use of low gelling/low melting temperature hydroxyethyl agarose, derivatives, such as SeaPlaque ® and SeaPrep ® agaroses, permits addition of temperature sensitive microorganisms to gel-forming solutions at temperatures well below those experienced with agars. Because of the advantages of agarose and its derivatives, it has become a matrix of choice for maintenance and cultivation of sensitive cells and other microorganisms.

The inhibitory effects of agar are well known among microbiologists. It is not unusual for bacterial, fungal, yeast, and other cells to flourish in liquid media, but then fail to grow, or at least grow considerably slower, on agar media. While other factors may contribute, the presence of the anionic polysaccharides in agar has been shown to be the major factor. For example, agarose preparations for Mengovirus plaque formation have been found to be essential, and for in vitro propagation of the spherule phase of *Coccidioides immitis* and culturing Mycoplasma species agarose is superior to agar. Discrepancies have repeatedly been shown to exist between minimum inhibitory concentrations of antibiotics against various microorganisms in nutrient broth compared with agar. It has been concluded that the anionic binding substituents in agar are responsible. With agarose, these are virtually absent, thereby substantially improving the growth efficiency of the microorganisms. Agarose is an ideal solidifying agent for assaying the antifungal activity of chemicals, and acidophilic, heterotrophic bacteria of acidic mine waters were able to be cultivated on solid nutrient media only if agarose was used as the gelling agent. MacKay describes a SeaPlaque® agarose overlay procedure for culturing genetically transformed yeast cells [MacKay, V. L., "Cloning of Yeast STE Genes in 2 μm Vectors", *Meth. Enzymol.*, 101, 325–343, 1983.]The use of an agarose coating in situ for infected leaves to retain fungal inoculum for further study also has been reported [Ryan, C. C., and Clare, B. G., "Coating of Leaf Surfaces With Agarose to Retain Fungal Inoculum in situ for Staining", *Stain Technol.*, 49, 15–18, 1974.] Further reported uses include: biotransformations using microbial cells encapsulated in agarose; continuous inversion of sucrose by agarose gel entrapped yeast cells; formation of proinsulin by agarose immobilized *Bacillus subtilis*: and using yeast cells entrapped in agarose in a process for continuous production of ethanol.

As a result of the unqualified success regarding plant protoplast cultivation on low gelling/low melting temperature agarose, SeaPlaque® agarose has become the international standard for such applications. Significant improvement was found in cloning efficiencies and cell division was induced in otherwise unresponsive systems. Using SeaPlaque® agarose it was possible to obtain high frequency maize callus colony formation from protoplasts plated on a nitrocellulose filter resting on a feeder cell-containing agarose layer. Other literature reports indicate the beneficial effects of agarose for plant protoplast cloning and cell regeneration including rice, hops, and alfalfa. Low gelling temperature agarose was the essential medium for stable transformation of soybean protoplasts with a kanamycin resistant gene using electroporation, and using the low gelling melting temperature SeaPlaque® agarose for tomato and potato protoplast cloning and plant regeneration, there has been reported up to 50-fold increased efficiencies with normal shoot formation from protoplast-derived cells.

In addition to the use of plant cells for genetic transformations and regeneration, their value as producers of valuable secondary metabolites has been recognized. In order to facilitate production, various plant cells have been immobilized by encapsulation in agarose prior to being introduced into bioreactors.

Viability retention of plant protoplasts encapsulated in agarose has been reported, and using lectins and ligands, there was developed a unique reversible process for immobilizing plant protoplasts on agarose beads. P NMR has been used to compare the metabolism of freely suspended plant cells and those encapsulated in agarose.

The beneficial effects observed and reported by scientists using agarose for cell culture are not limited to microbial and plant cell applications. As early as 1968, agarose was reported to be superior to agar for studying the transformation of BKH2l cells, which was related to the presence of acidic polysaccharides in the agar. Studies showed that adenovirus-transformed rat embryo cells rapidly acquired the ability to grow in agarose, whereas they would not grow in agar until after prolonged passage. In 1974, there was reported a method for cloning anchoragedependent cells in agarose. As a result of experiments assaying the growth of 19 cell lines, it was reported that anchorage-independent cell growth in agarose is a more definitive indicator of tumorgenicity than growth in agar. It also has been found that the efficiency of colony formation of EBV-transformed mononuclear leukocytes depended, at least partially, on the type of agarose used. SeaPlaque® agarose was very effective.

The low-gelling/low-melting temperature hydroxyethyl agarose derivatives, SeaPlaque® and SeaPrep® agaroses were found to have unique properties, in addition to their exceptionally high degree of purity, which make them especially useful for animal cell culture. SeaPlaque® agarose, with its gelling temperature of about 28° C., permits additions to and incubation of the sol at the physiological temperature of 37° C. Cooling the agarose solution to below 28° C. causes it to gel. Since the remelt temperature is about 65° C., the mixture can be reincubated as a gel at 37° C. or below, a necessity for forming beads with entrapped cells and cellular materials. The more highly derivatized hydroxyethyl agarose, such as SeaPrep® agarose exhibits even lower gelling and melting temperatures, 15° C. and <50° C. respectively, enabling some biological materials to be recovered from the gel by melting it. The lower the gelling and melting temperatures, however, the lower the gel strength—a factor that must be considered when designing experiments.

Optical clarity of SeaPrep® agarose is excellent, particularly when quickly gelled into small beads, enabling microscopic observation of growing colonies. SeaPrep® agarose gels, at concentrations of 0.5 to 0.75% have been reported to support high efficiency growth of NSI clones, and it has been found that at 0.86% gel concentration, nearly theoretical cloning efficiency was obtained for murine hybridoma cells. Beads formed from the weak SeaPrep® agarose gel can be disrupted easily, allowing transfer of the viable cells by pipet to liquid culture media for subsequent growth.

Representative applications of the various types of agarose to animal cell culture include: cloning of human lymphoid cells without feeder layers, collagen expression by chondrocytes, proteoglycan synthesis by articular bovine chondrocytes, B-cell cloning, T-cell cloning, human natural killer cell growth, early chick embryonic cell cloning, production of transforming growth factor by chemically transformed cells, assay of transforming growth factor using rabbit articular chondrocytes, studying the selective inhibitory effect of human interferon on the agarose clonability of tumorderived lymphoid cell lines, human monoclonal autoimmune antibody production, culturing hamster pancreatic acinar tissue, stabilizing isolated molluscan neurons, clonal transformation of human leukocytes by Epstein-Barr virus, demonstrating chemical mutagenesis at the phosphoribosyltranferase locus in cultured human lymphoblasts, studying the effect of retinoic acid on the growth and morphology of a prostatic adenocarcinoma cell line, culturing human hybridomas secreting antibody to tetanus toxoid, culturing human head and neck squamous cell carcinoma stem cells, studying the in vitro proliferation of a human urinary transitional cell carcinoma cell line, tumor stem cell cloning, culturing human breast carcinoma cell lines in serum-free medium, assaying tumorgenicity of primate cell lines, detecting human renal cell carcinoma, monitoring tumor necrosis factor production and purification, and in vitro chemotherapy sensitivity testing of human renal cell carcinoma.

Cell growth optimization in agarose include: determining the effect of agarose concentration on the cloning efficiency of a series of established human cell lines, studying physical and nutritional factors in gel culture of mammalian cells; and developing a method for the in vitro cloning of tumor stem cells so they could be used for chemotherapeutic drug sensitivity testing.

Animal cells are being used in bioreactors to produce important pharmaceutical products. In a recent development, immobilizing the cells by encapsulating them in agarose, has proven to be beneficial. There is a report of entrapped hybridoma cells in SeaPlaque ® agarose for the production of monoclonal antibodies, and of designing a laboratory fermentor system to use the encapsulated hybridoma cells. There also has been reported the use of agarose to encapsulate insulinproducing islet of Langerhans cells, the ultimate goal being transplantation. A good review of the available methods for immobilizing animal cells can be found in Nilsson, K, *Methods for Immobilizing Animal Cells*, "Trends Biotechnol." 5:73-78 (1987).

Citations to reports of the above research can be found in "The Agarose Monograph", 4th ed., FMC Corp. pub. (1988).

To facilitate visual observation of cell cultures or other aspects of incorporated biological material, the beads produced according to this invention should have a regular shape, ideally spherical, discoidal, or toroidal. It is particularly important that tails, skirts, or other fragile projections of the gel are avoided, as well as that the face of the formed bead in contact with a receiving surface (when one is employed) be as smooth as possible. To achieve this, in those embodiments in which an agarose/broth mixture is dropped on a surface, the receiving surface should be hydrophobic, smooth, and preferably sterilizable so as to permit its continued use. Thus, when used, the surface should be sufficiently hydrophobic to prevent its wetting, so that the attraction of the agarose/broth mixture for itself should be greater than the attraction of the agarose mixture for the surface. This can most easily be defined in terms of the drop/surface contact angle which, for the purposes of this invention is defined as the angle between the liquid and the surface at the outermost point of contact, measured in relation to a perpendicular to the surface at that point. Thus, the more the surface is wetted, the higher the contact angle, a perfectly wetting non-bead forming substance having a theoretical angle of 0°, and a perfect sphere having a theoretical angle of 180°. A contact angle on a level horizontal surface of 45° or greater is acceptable for this invention and defined herein as "high hydrophobicity", 90° being preferred and defined herein as "very high hydrophobicity". None of the beads produced according to this invention had a contact angle greater than 90°, although such remains theoretically possible. On an inclined surface, the forward (lower edge) contact angle usually will be more than 90°, and greater than the trailing (upper edge) contact angle. Since the length of a bead tail should be kept to a minimum, it is desirable that the agarose/broth mixture have sufficient cohesiveness to minimize tail formation in the time it takes for the agarose/broth mixture to gel or at least for the drop to become sessile when the surface is inclined. For explanations of contact angles, reference is made to: P. C. Hiemenz "Principles of Colloid and Surface Chemistry", Marcel Dekker (pub.), N.Y., (1977), at pages 228-231; Kirk-Othmer "Encyclopedia of Chemical Technology" 3d ed., Wiley & Sons (pub.), N.Y., (1977), at volume 22 pages 340-341; and A. W. Adamson "Physical Chemistry of Surfaces", 3d ed., Wiley & Sons (pub.), N.Y., (1975), at pages 342-347.

The "cohesiveness" of the agarose/broth mixture results from a combination of (a) the particular agarose used, (b) the concentration of the agarose as a sol (aqueous solution), and (c) the degree dilution of the agarose aqueous solution by admixture of the biological material-containing aqueous solution (broth).

Hydrophobic surface materials that are suitable for receiving dispensed drops include: fluorinated ethylene-propylene copolymers, such as Teflon ® FEP fluorocarbon resins [a product of Du Pont]; tetrafluoroethylene copolymers with ethylene, such as Tefzel TM resins [a product of Du Pont]; tetrafluoroethylene copolymers with perfluorovinyl ethers; butyl rubber silicone polymers, polypropylene; polyethylene terephthalate; and the like. This invention is not limited to a particular hydrophobic surface, and other surfaces which are smooth, hydrophobic, and readily release the gelled beads also may be used, including substrates of any nature with a coating of a biologically inert wax whose melting point is sufficiently above 40° C. so that none of such wax is incorporated within the formed bead. In addition to being hydrophobic and smooth, the receiving surface must be sterilizable (to prevent bead contamination) without undergoing surface deformation.

The temperature at which the beads are formed can vary within certain limited ranges. Thus, it is a basic and critical requirement of this invention (except for Embodiment V) that the bead formation temperature is lower than the temperature at which the biological material to be incorporated is destroyed or substantially impaired in its desired ability to function. The upper bead formation process temperature therefore, can be 45° C. or less, but is preferably 40° C. or less, more preferably 37 C. or less, most preferably 30° C. or less. There is no easily defined lower bead formation process temperature, except that such lower temperature should not be so low that the biological material to be incorporated is destroyed or substantially impaired in its desired ability to function. No advantage is obtained in a bead formation process temperature lower than that at which beads form within ~300 seconds of the discharge of the drop of agarose/broth mixture. Thus, although less critical than its upper temperature, the bead formation temperature may be as low as slightly above the freezing point of water (0° C.), such as 0.5° C., preferably as low as 5° C., more preferably as low as 10° C.

The desired gelling temperature may be achieved by cooling the hydrophobic surface onto which the agarose/broth drops are dispensed, optionally accompanied by cooling the ambient atmosphere; or when no such surface is used, by cooling the atmosphere alone, the gas stream, etc.

The "cooling means" employed in this invention is not limited to a particular device or embodiment, but includes any means for achieving the desired cooling of the hydrophobic surface, atmosphere, gas stream, etc.

Such means include: contacting the distal side of the hydrophobic surface with stationary or moving cold water or other fluid; conducting the entire procedure in an enclosed refrigerated atmosphere; cooling the hydrophobic surface by rapid evaporation of a fluid from its distal side; passing a pressurized, expanding gas such as from a container of liquefied nitrogen across the distal side of the hydrophobic surface and/or directly across the dispensed agarose/broth mixture; cooling the gas stream by refrigeration, evaporation, or rapid expansion; and the like.

The time for completion of the inventive process is not at all critical where the hydrophobic surface is horizontal, and need be shortened only where the bead has a tendency to form a tail or similar detachable projection, such as where the hydrophobic surface is inclined. Generally, process time is temperature dependent, lower temperatures resulting in quicker gelling.

The proportions of agarose (powder) to water to biological material to be incorporated cannot be quantified per se, since they will depend upon: (a) the particular agarose utilized; (b) the gel strength needed for the particular use of the beads after formation; (c) the particular nature of the biological material to be incorporated; and (d) the amount of carrier liquid (broth) and concentration of the biological material therein. However, these parameters can easily be determined by one of ordinary skill in the art, without undue experimentation, by using proportions of agarose powder and total liquid anticipated, to achieve gel strengths in accordance with the procedure in the "Agarose Monograph", supra, which is incorporated herein by reference for this purpose.

For the purposes of this invention, the gel strength therefore is the only parameter that needs to be quantified. Agarose beads incorporating biological material may be varied in gel strength based upon the nature of the incorporated material and, to a lesser extent, the particular manner in which the beads are to be utilized. A gel strength of $50g/cm^2$ minimum up to $1,000g/cm^2$ maximum is suitable, a gel strength of $125°-250g/cm^2$, especially $125-175g/cm^2$, being preferred for mammalian cells, protoplasts, and other more fragile biological material and a strength of $250-1000g/cm^2$, especially $500-1000g/cm^2$ being preferred for bacteria, plant cells, enzymes, and other less fragile biological material. Considerably higher gel strengths, of the type obtainable with non-agarose gels and with agarose outside the scope of this invention is undesirable, since the incorporated biological material must be unhindered in its growth, and/or its expression of desired by-products, and/or its access to nutrient media or fluids with which it otherwise interacts. Gel strength is of significantly less importance where no biological material is to be incorporated.

EXAMPLES OF PROCESS EMBODIMENTS ACCORDING TO THIS INVENTION

Example 1 (illustrative)

Preparation of Agarose Beads Using a Polypropylene Perforated Sheet with Staggered Centers Procedure:
1) Prepare a 1.75% by weight concentration Sea-Prep ® agarose aqueous solution and let it cool to 37° C. Admix the biological material (aqueous broth or concentrated pallet) to be incorporated, so that the admixture has an agarose concentration of 1 to 4% by weight.
2) Dip a polypropylene shaft (hydrophobic surface) with 3/32 inch (~0.24 cm) circular perforations into the agarose/broth mixture and swirl.
3) Lift the perforated sheet out of the beaker and allow excess agarose/broth mixture to drain, optionally wiping it dry with a lint-free material.
4) Cool the perforated sheet, such as by placing it upright in a freezer (temp ~ −10° C.) for 1 minute (caution—if the agarose/broth mixture remains in the freezer for more than 3 minutes it will start to freeze), to form beads.
5) Attach one end of surgical tubing to an air pressure source. Attach a pipette (5.75 inch (~14.6 cm) Pasteur, or the like) to the other end (Clamp if necessary.)
6) Remove the perforated sheet from the freezer and hold it above a collecting dish.
7) Hold the pipette 1 or 2 inches (~2.5 to 5 cm) above the perforated sheet and turn on the air pressure. The pressure should be high enough to blow the agarose/broth mixture beads out of the sheet and into the collecting dish typically ~13 psi (one psi equals $7.03 \times 10^2$ Kg/m$^2$).
8) Continue a positive pressure by making sweeping motions across the face of the perforated sheet, to blow out the rest of the agarose/broth mixture beads (in discoidal configuration) into the collecting dish.

EXAMPLE 2 (illustrative)

Formation of Beads on a Very Cold, Hydrophobic Surface.

Procedure

Small drops of water of approximately the same size as the desired beads (i.e. 1-3 mm) will form approximately hemispherical beads on a hydrophobic receiving surface. If the surface is very cold (~0° C.) and the bead volume very small (~10 μL), then a gelation of even a low gelling temperature agarose (15-28° C. @1%) will occur quickly, even if the agarose/broth admixture when applied is at mammalian physiological temperature ~37° C.

One can employ simultaneous aqueous agarose/broth droplet formation at many sites across a cold hydrophobic receiving surface followed by sweeping the surface clean manually or with a mechanical wiper so a second batch of beads can be formed, after the first drops have gelled into agarose beads.

EXAMPLE 3 (illustrative)

Preparation of Agarose Beads Using a Cylinder with Internal Cooling Means

Procedure
1) Prepare an agarose/broth solution and let it cool to 37° C. in the same manner as in Example 1.
2) Fill a syringe equipped with a 21 gauge blunt needle with the agarose/broth solution and attach it to a manual or automatic, single or multiple dispenser.
3) Fill a cylinder with an integral or laminate hydrophobic surface (such as a metal can) with ice and attach it horizontally through its central axle to a mechanical power source such as an electric motor.

4) Position the syringe ~1 cm above the top of the cylinder, parallel to the central axis if a linear multiple dispenser.
5) Set the dispenser with drops coming out at 6 second intervals.
6) Turn on the dispenser and manually rotate the cooling wheel approximately 1 cm counter clockwise after every drop or set of drops.
7) Using a laboratory tissue, wipe the hydrophobic surface of the cooling wheel so that it is fairly dry before the agaros is dispensed on it.

Example 4 (actual)

Upscaling Agarose Production on a Hydrophobic Surface

The following procedure is a composite of repeated actual laboratory experiments, which were run with agarose alone; i.e. without admixed biological material. Since the physical properties of an agarose/biological material mixture would not significantly differ, (excepting the survivability of the biological material), the procedure also demonstrates the feasibility of forming beads incorporating biological material.

Procedure
1) Prepare a 1.75% SeaPrep ® agarose solution and let it cool to 37° C.
2) Set cooling chamber at ~80° C.
3) Cut a 30 cm sheet of a hydrophobic paraffincoated flexible film sheet and lay it flat on the surface of the cooling chamber. Allow a little excess film to hang over the edge of the cooling chamber and into a dish of distilled H$_2$O.
4) Set the cooling chamber temperature gauge to 4° C. and allow the slide to cool to temp.
5) Wipe the film sheet with a laboratory tissue to remove any air bubbles which may be trapped under the sheet.
6) Using a "plant mister," spray the surface of the slide with distilled H$_2$O (approx. 2 sprays), just enough to have an even coat of little water droplets on the film surface.
7) Fill a syringe equipped with a 21 gauge needle with the 1.75% SeaPrep agarose solution.
8) Hold the syringe about 6 cm above the top of the slide and dispense the agarose onto its surface.
9) The agarose should hit the surface of the slide and slowly travel to the bottom, where it will be collected in the water bath.

Example 5 illustrative

The blast-of-cold-gas approach

Even though gelation of "sprayed" beads is complicated by the low gelling temperature of the agarose(s) which must be used to maintain cell viability (at 37° C.), it is nevertheless conceivable that such a process might be developed. For example, to facilitate cooling, each agarose sol droplet (automated syringe, etc.) might be injected into a chilled gas (spray freeze: nontoxic, odorless) which would make gelation almost instantaneous. To further facilitate gelation, a distance could be provided for air/gas cooling before contact with the collection solution (4° C.) and other beads.

Example 6 (actual)

Incorporation of living cells into agarose beads invention) and alginate beads (comparison)

Preparations
1) Hydrophobic Surface: A 0.2 mm thick sheet of polyethyleneterphthalate film (7.6×7.6 cm). known to have hydrophobic surface (contact angle of 59°-76° with water), was placed in a petri dish, hydrophobic side on top. The dish was then placed 35 cm below a U.V lamp (G.E. type G8T5) for 15 minutes. The film that was not used immediately, was stored at −20° C. in enough 70% ethanol to cover the film completely.
2) Hydrophobic Oil: 200 mL of food grade corn oil (Mazola TM) was placed in a clean 300 mL beaker and autoclaved in the standard manner [15 psi, 15 mm @225° F. (101° C.)].
3) Agarose: Previously sterile filtered and preliquefied hydroxyethyl agarose (SeaPrep ®; BRE-293) was liquefied in a hot water bath (90° C.) and then stored at 37° C.

Alcinate: Two grams of alginate powder (Keltone TM LV #87254; BRE-137) was dispersed in 100 mL of cold distilled water and stirred until dissolved. The 2% alginate solution was then sterilized by autoclaving [15 psi, 15 mm, 225° F. (121° C.)] and stored under refrigeration (4° C.) until used.
5) Cell Preparation: HT-29 Human coloncarcinoma cells (~$10^7$ cells in 10 mL suspension) were obtained from the American Type Culture Collection, Rockville, Md. The 10 mL cell suspension was treated with trypsin according to standard tissue culture protocol, washed with Eagle's Medium Essential Medium (MEM) and then centrifuged to form a pellet (~$5 \times 10^6$ cells).

1% Alginate Beads
1) The several mls of 2% alginate stock solution were warmed to 37° C. and diluted with sterile water to a 1% concentration and reequilibrated to 37° C.
2) Using a 10 mL syringe equipped with an 18 gauge needle, 50 drops (1 mL) of the 1% alginate solution were added to the washed cell pellet ($5 \times 10^6$ cells) and the cells resuspended in the alginate.

The cell/alginate suspension was taken back up in the syringe and dispensed drop-wise into a stirred sterile solution of CaCl$_2$ (100 mL). A total of 50 drops were dispensed, each droplet forming a bead containing ~$10^5$ cells. Care was taken to place the droplets so as to prevent droplets from colliding before bead formation could occur.
4) After five minutes, the beads were sufficiently gelled that the supernatant CaCl$_2$ could be decanted and the cell entrapment beads washed (2×) with 25 mL of serum-free Eagle's Medium Essential Medium (MEM).
5For cell culture, the alginate beads were placed in Eagle's MEM which contained the following additives: FBS (10%), glutamine (2 mM), penicillin (250 U/mL), streptomycin (250 ug/mL) and nonessential amino acids (Sigma, 10 mm). The beads were then incubated at 37° C. and 5% CO$_2$ until they were assayed.
6) The alginate entrapment beads represented a control for comparison with the agarose bead casting on the hydrophobic surface. Alginate entrapment is well accepted as a technique for immobilizing and growing anchorage-independent mammalian cells such as transformed HT-29 cells.

Agarose Bead Formation in Oil:

1) One mL of CelPrep TM agarose sol (1.75%), equilibrated at 37° C., was withdrawn by means of a sterile 10 mL syringe equipped with a sterile 18 gauge needle. "CelPrep" is a trademark of the BioProducts Group, Marine Colloids Division, of FMC Corporation.
2) Fifty drops (i.e. 1 mL) of CelPrep agarose sol were dispensed on a washed (MEM) cell pellet containing approximately $5 \times 10^6$ HT-29 cells, prepared as described above.
3) The HT-29 cells were then gently mixed with the syringe needle until they were uniformly distributed.
4) Fifty drops of the cell/agarose suspension, each drop containing approximately $10^5$ cells were dispensed into 40 mL of chilled Mazola ® corn oil (4° C.) contained in a small crystallizing dish.
5) The drops were dispensed slowly from a height of 4 cm and spaced in the chilled oil so that they did not coalesce before gelation.
6) Five minutes after the last drop was dispensed, the oil containing dish was tapped to facilitate settling of the agarose beads on the bottom.
7) The supernatant oil was decanted and the cells washed with 25 mL of phosphate-buffered saline (PBS).
8) The washed agarose beads were then transferred to a clean beaker and washed repeatedly ($3 \times 25$ mL) to remove the residual oil.
9) After decanting the third PBS wash, the beads were suspended in 25 mL of serum-free Eagle's MEM and allowed to stand for 10 minutes.
10) The agarose beads were then incubated in Eagle's MEM containing 10% PBS, glutamine, penicillin, streptomycin and amino acids as described above for the alginate beads.
11) Incubation was conducted at 37° C. and 5% $CO_2$ and the gel growth periodically assayed using the MTT assay.

Note: The MTT assay was used to infer cell proliferation in each entrapment matrix and/or procedure. The MTT procedure is a well-accepted means of indirectly measuring cell proliferation as a function of the reduced MTT dye (blue) produced. The assay is conducted as follows:

i) Using the large end of a pasteur pipette, transfer one bead to a 16 mm diameter well.
ii) Add 5 $\mu$g of MTT reagent [3-(4,5-Dimethylthazol-2yl)-2,5-diphenyl-tetrazolium bromide] in 10 $\mu$L plus 200 $\mu$L serum free MEM.
iii) Swirl the plate to mix the reagents.
iv) Incubate at 37° C. for two hours.
v) Aspirate the supernatant liquid.
vi) Add 200 $\mu$L of solution C (isopropanol +0.04 N HCl).
vii) Swirl to mix.
viii) Incubate at 37° C. for 24 hours.
ix) Remove 100 $\mu$L of blue solution to a 96 well Elisa Plate.
x) Read OD. at 570 nm.

MTT Reagent Source: Chemicon; El Segundo, Calif.

Agarose Bead Formation on Hydrophobic Surface

1) Fifty drops of the equilibrated (37° C.) CelPrep TM Agarose sol (1.75%) were dispensed on a washed (MEM) pellet of HT-29 cells ($\sim 5 \times 10^6$). Prepared as described above.
2) The HT-29 cells were resuspended in the agarose sol using a sterile 10 mL syringe equipped with a sterile 18 gauge needle.
3) The cell/agarose suspension was taken back up in the syringe and dispensed, dropwise on the chilled hydrophobic side of a sheet of sterile GelBond ® film. The sterile GelBond was placed in a petri dish partially filled with ice. To minimize extraneous contamination, this operation was conducted in a laminar flow hood.
4) Each drop was deposited on the hydrophobic surface from a distance of 5 mm above it. The drop was observed to bead up immediately and rapidly begin to gel.
5) After five minutes, the agarose beads were easily flushed off the hydrophobic surface with a stream of complete MEM medium (i.e. containing 10% FCS, glutamine etc.).

Note: There was no need to wash the beads, thereby making the procedure much simpler. Also, the rate of gelation was conveniently controlled by the rate of cooling (i.e. to be $\leq 1$ mm/bead) and the size of each droplet.

6) The agarose beads were then incubated in complete MEM medium at 37° C. and 5% $CO_2$.
7) Cell proliferation was monitored using the MTT assay.

Experimental Data for Examole 6

A comparison was made between the proliferation rates of HT-29 cells incorporated in: (A) agarose beads prepared according to this invention; (B) agarose beads formed in oil as known in the art; and (C) alginate beads, as known in the art. The results are shown in the following

TABLE

| Experiment | Percentage of day zero after day | | | | | | | | |
|---|---|---|---|---|---|---|---|---|---|
| | 1 | 2 | 3 | 4 | 5 | 6 | 7 | 8 | 9 |
| (A) agarose [invention] | 181 | — | 234 | 320 | — | — | 318 | — | 233 |
| (B) agarose-in-oil [prior art] | 130 | — | 185 | 233 | — | — | 171 | — | 184 |
| (C) alginate [prior art] | 115 | — | 75 | 99 | — | 145 | 155 | — | 159 |

The above data indicates a desirable persistently higher proliferation rate for cells incorporated in beads according to this invention. The superiority of agarose over alginate is illustrated by comparing A or B with C. The superiority of the inventive process over the prior art agarose process is illustrated by comparing A with B.

We claim:

1. A method for forming agarose beads incorporating biological material at least partially labile at above 40° C. comprising:
   A) forming an aqueous solution consisting essentially of an agarose which gels at a temperature of about 40° C. or less;
   B) cooling the agarose solution to 40° C. or less while maintaining it in liquid form;

C) admixing an aqueous broth containing biological material which is at least partially labile at above 40° C. with the gel solution, to form a liquid agarose/broth mixture;

D) forming bead-size portions of the liquid agarose/broth mixture;

E) contacting said portions with a cooled atmosphere, gas, and/or smooth hydrophobic surface and maintaining such contact until said portions gel into formed agarose beads containing biological material; and F) collecting the formed beads.

2. The method of claim 1 wherein said agarose is derivatized and gels at a temperature of about 30° C. or less.

3. The method of claim 1 wherein the proportions of agarose to biological material to water is such as to result in a gel strength of about 50–1,000 g/cm2.

4. The method of claim 1 wherein the biological material is of mammalian origin.

5. The method of claim 4 wherein the proportions of agarose to biological material to water is such as to result in a gel strength of about 125–250 g/cm2.

6. The method of claim 1 wherein the formed beads have an average weight of about 10 micrograms to 50 milligrams.

7. The method of claim 1 wherein the formed beads have an average weight of about 5-20 milligrams.

8. The method of claim 1 wherein:
said agarose is derivatized and gels at a temperature of about 30°0 C. or less;
the proportions of agarose to gel to water is such as to result in a gel strength of about 125 to 250 g/cm2;
the biological material is of mammalian origin; and
the formed beads have an average weight of about 5 to 20 milligrams.

9. A method for forming agarose beads comprising:
A) forming an aqueous agarose solution;
D) forming bead-size portions of said agarose solution;
E) contacting said portions with a cooled atmosphere, gas, and/or smooth hydrophobic surface and maintaining such contact until said portions gel into formed agarose beads; and
F) collecting the beads.

10. The method of claim 1 or 9 wherein discoidal beads are formed by effecting:
step D) by immersing a sheet of smooth hydrophobic planar material perforated with uniformly sized round holes, whose diameter is approximately that of the beads to be formed, into said agarose/broth mixture, and then withdrawing the sheet so that portions of said mixture are retained within said holes;
step E) by placing the sheet containing the retained mixture in a cooled atmosphere; and
step F) by subjecting the gelled beads to a positive pressure on one side to force the beads out of the holes and into a container.

11. The method of claim 1 or 9 wherein hemispheroidal beads are formed by effecting:
step D) by dispensing separate small drops of agarose/broth mixture from a dispensing means positioned proximately above the top of a horizontal hydrophobic surface;
step E) by cooling said surface; and
step F) by removing the beads from said surface, and directing them into a container.

12. The method of claim 11 wherein said removing in step F) is effected by gently scraping said surface with a doctor blade.

13. The method of claim 11 wherein said removing in step F) is effected by inclining said hydrophobic surface sufficiently for said beads to slide or tumble off under force of gravity.

14. The method of claim 11 wherein said removing in step F) is effected by employing a flexible hydrophobic surface and flexing said surface sufficiently to loosen said beads, and then inclining said surface sufficiently for said beads to slide or tumble off under force of gravity.

15. The method of claim 11 wherein said removing in step F) is effected by employing a flexible hydrophobic surface and forming said surface into a chute or funnel to loosen said beads, and then directing said chute or funnel into said container.

16. The method of claim 11 wherein said removing is assisted by a directed water wash.

17. The method of claim 12 wherein said removing is assisted by a directed water wash.

18. The method of claim 13 wherein said removing is assisted by a directed water wash.

19. The method of claim 14 wherein said removing is assisted by a directed water wash.

20. The method of claim 15 wherein said removing is assisted by a directed water wash.

21. The method of claim 1 or 9 wherein hemispheroidal beads are formed by effecting:
step D) by dispensing separate small drops of agarose/broth mixture from a dispensing means positioned proximately above the highest point of a cooled cylindrical hydrophobic surface disposed with a horizontal central axis;
step E) by permitting said drops to contact said surface at its highest point, and to remain in such contact until the agarose/broth mixture gels into beads, while rotating the cylinder about 90° around its axis; and
step F) by permitting the gelled beads to fall into a collecting container by force of gravity.

22. The method of claim 21 wherein said hydrophobic surface is cooled by utilizing a hollow cylinder, and contacting the cylinder interior with a cold fluid.

23. The method of claim 21 wherein step F) further comprises biasing a fixed doctor blade against the cylinder hydrophobic surface, by the rotation of said cylinder.

24. The method of claim 22 wherein step F) further comprises biasing a fixed doctor blade against the cylinder hydrophobic surface, by the rotation of said cylinder.

25. The method of claim 1 or 9 wherein spheroidal beads are formed by effecting:
step D) by dispensing separate small drops of agarose/broth mixture from a dispensing means, so that they free fall;
step E) by directing an upward flowing cooling gas around said drops, with sufficient force so that said drops are at least partially suspended in said cooling gas until they gel into beads, and
step F) by permitting the suspended beads to fall into a collecting container at a velocity governed by the force of said upward flowing cooling gas.

26. The method of claim 25 conducted within a cooling tower.

27. The method of claim 26 run as a batch method, by interrupting the flow of cooling gas and the dispensing of said drops periodically.

28. The method of claim 26 run as a continuous method, by controlling the flow of cooling gas so that the gelling of the drops into beads is approximately simultaneous with their descent to the bottom of the cooling tower.

29. An agarose bead incorporating biological material at least partially labile at above 40° C., formed by the method of claim 1.

30. Agarose beads formed by the method of claim 9.

* * * * *